(12) United States Patent
Peyman

(10) Patent No.: US 7,220,278 B2
(45) Date of Patent: *May 22, 2007

(54) TELEDIOPTIC LENS SYSTEM AND METHOD FOR USING THE SAME

(75) Inventor: Gholam A. Peyman, New Orleans, LA (US)

(73) Assignee: Minu Telesystems LLC, Pittsboro, NC (US)

(*) Notice: Subject to any disclaimer, the term of this patent is extended or adjusted under 35 U.S.C. 154(b) by 158 days.

This patent is subject to a terminal disclaimer.

(21) Appl. No.: 10/600,371

(22) Filed: Jun. 23, 2003

(65) Prior Publication Data

US 2004/0167623 A1 Aug. 26, 2004

Related U.S. Application Data

(63) Continuation-in-part of application No. 10/455,788, filed on Jun. 6, 2003.

(60) Provisional application No. 60/449,618, filed on Feb. 26, 2003.

(51) Int. Cl.
*A61F 2/16* (2006.01)

(52) U.S. Cl. ............... 623/6.28; 623/6.36; 623/6.34

(58) Field of Classification Search ...... 623/6.23–6.37, 623/FOR. 105

See application file for complete search history.

(56) References Cited

U.S. PATENT DOCUMENTS

| | | | |
|---|---|---|---|
| 4,074,368 A | 2/1978 | Levy, Jr. et al. | |
| 4,581,031 A | 4/1986 | Koziol et al. | |
| 4,666,446 A * | 5/1987 | Koziol et al. | 623/6.33 |
| 4,718,418 A | 1/1988 | L'Esperance | |
| 4,840,175 A | 6/1989 | Peyman | |
| 4,892,543 A | 1/1990 | Turley | |
| 4,932,971 A | 6/1990 | Kelman | |
| 4,957,506 A | 9/1990 | Mercier | |

(Continued)

FOREIGN PATENT DOCUMENTS

WO  WO 94/07435  4/1994

OTHER PUBLICATIONS

English translation of DE 195 01 444 A1 (Mitschischek).*

*Primary Examiner*—David H. Willse
(74) *Attorney, Agent, or Firm*—Bell, Boyd & Lloyd LLP

(57) ABSTRACT

An intraocular lens system for implantation in the eye to modify the lens system of the eye comprising the cornea and the natural or existing artificial lens in the eye, and a method for using the same. The system and method comprises a lens having a high minus portion, adapted to be implanted in the eye to create a lens system that functions as a teledioptic lens system which, when used without an external lens, provides unmagnified and peripherally unrestricted vision and which, when used with an external lens, provides magnified and peripherally restricted vision to correct for macular degeneration. The lens can be attached to the iris, to a portion of the iris that was removed by iridectomy, or can be implanted in the cornea. The lens can also include a plus portion that is surrounded by the high minus portion. The high minus portion is preferably about one to about three millimeters in diameter, and can have an outer perimeter with no surrounding material or can be surrounded by a plus, minus or toric lens.

20 Claims, 6 Drawing Sheets

U.S. PATENT DOCUMENTS

| | | |
|---|---|---|
| 4,994,058 A | 2/1991 | Raven et al. |
| 5,030,231 A | 7/1991 | Portney |
| 5,098,444 A | 3/1992 | Feaster |
| 5,133,745 A | 7/1992 | Falcetta et al. |
| 5,180,389 A * | 1/1993 | Donn et al. ............... 623/6.35 |
| 5,201,762 A | 4/1993 | Hauber |
| 5,336,261 A | 8/1994 | Barrett et al. |
| 5,354,335 A | 10/1994 | Lipshitz et al. |
| 5,358,520 A | 10/1994 | Patel |
| 5,366,502 A | 11/1994 | Patel |
| 5,391,202 A * | 2/1995 | Lipshitz et al. ............ 623/6.34 |
| 5,476,515 A | 12/1995 | Kelman et al. |
| 5,607,472 A | 3/1997 | Thompson |
| 5,814,103 A | 9/1998 | Lipshitz et al. |
| 5,876,442 A | 3/1999 | Lipshitz et al. |
| 5,928,283 A | 7/1999 | Gross et al. |
| 6,007,579 A | 12/1999 | Lipshitz et al. |
| 6,066,171 A | 5/2000 | Lipshitz et al. |
| 6,187,042 B1 | 2/2001 | Sheets, Jr. et al. |
| 6,197,035 B1 | 3/2001 | Loubens et al. |
| 6,197,057 B1 | 3/2001 | Peyman et al. |
| 6,357,875 B1 | 3/2002 | Herrick |
| 6,358,280 B1 | 3/2002 | Herrick |
| 6,569,199 B1 | 5/2003 | Dotan et al. |
| 6,596,026 B1 | 7/2003 | Gross et al. |
| 2003/0014107 A1* | 1/2003 | Reynard .................... 623/6.24 |
| 2006/0004446 A1* | 1/2006 | Aharoni et al. ............ 623/6.13 |

* cited by examiner

TELEDIOPTIC LENS SYSTEM AND METHOD FOR USING THE SAME

This application claims the benefit under 35 U.S.C. § 119(e) of provisional patent application Ser. No. 60/449,618, filed Feb. 26, 2003, the entire content of which is incorporated herein by reference, and is a continuation in part of application Ser. No. 10/455,788, filed Jun. 6, 2003 and entitled TELEDIOPTIC LENS SYSTEM AND METHOD FOR USING THE SAME, the entire content of which is incorporated herein by reference.

CROSS REFERENCE TO RELATED APPLICATIONS

This application is related to U.S. Pat. No. 6,197,057 to Peyman et al. entitled "LENS CONVERSION SYSTEM FOR TELEDIOPTIC OR DIFFRACTIVE CONFIGURATIONS", and copending U.S. application Ser. No. 10/356,730 entitled "SUBEPITHILIAL IMPLANT AND METHOD OF TREATMENT OF PRESBYOPIAN AND OTHER REFRACTIVE ERRORS", the entire contents of both of which are incorporated herein by reference.

FIELD OF THE INVENTION

The present invention generally relates to a lens system for correcting vision in the eye. More specifically, the present invention generally relates to a dual lens system that provides telescopic vision to an eye to correct the vision thereof.

BACKGROUND OF THE INVENTION

A normal ametropic eye includes a cornea, lens and retina. The cornea and lens of the normal eye cooperatively focus light entering the eye from a far point, i.e., infinity, onto the retina. However, an eye can have a disease known as macular degeneration which can greatly degrade vision.

Macular degeneration has become one of the leading causes of blindness in adults. This disease affects the central retinal area known as the macula which receives light focused by the cornea and lens and acute vision. Macular degeneration can lead to a gradual or sudden loss of vision to the level of 20/200 or less. Commonly, loss of vision only affects the central retinal area of about 0.25 to 4 square millimeters, and does not usually progress beyond this area, thereby leaving 95–99% of the retina unaffected. Thus, reading and driving vision can be lost, while peripheral vision remains intact.

U.S. Pat. Nos. 4,666,446 and 4,581,031, both to Koziol and Peyman, and both of which are incorporated by reference herein, each disclose intraocular lenses which are implanted in the eye in place of the natural lens to redirect the rays of light to minimize the adverse affect on vision caused by the macular degeneration of the eye. For example, U.S. Pat. No. 4,666,446 discloses an intraocular lens comprising a first portion including a diverging lens and a second portion including a converging lens. The converging lens provides the eye with substantially the same focusing ability of the natural lens prior to implantation of the intraocular lens. Thus, the eye will have decreased visual acuity due to the macular degeneration, but will also have unrestricted peripheral vision. The diverging lens, on the other hand, when combined with a converging lens positioned outside of the eye (e.g., a spectacle lens), provides a magnified image with increased visual acuity but a restricted visual field. Therefore, this type of intraocular lens creates teledioptic lens system, which provides the patient with the choice of unmagnified but peripherally unrestricted vision or magnified but peripherally restricted vision.

U.S. Pat. No. 4,581,031, discloses an intraocular lens including a convex portion and a prismatic portion. The combined convex/prismatic lens directs rays of light away from the center of the retina that has been damaged by macular degeneration, and focuses those rays onto an undiseased area of the retina, thus providing greater visual acuity.

As discussed above, U.S. Pat. Nos. 4,666,446 and 4,581,031 clearly disclose that it is known to use particular types of intraocular lenses in place of the natural lens to reduce the adverse affect of macular degeneration on vision. However, neither of the patents disclose that it is known to use an intraocular lens to modify an existing lens system in the eye, comprising the cornea and a natural or artificial lens already present in the eye, to create a lens system having the prismatic or teledioptic capabilities discussed above to correct for macular degeneration in the eye.

U.S. Pat. Nos. 5,098,444, 5,366,502, 5,358,520, and 4,932,971, as well as world patent application WO 94/07435, each disclose that it is known to attach a supplemental intraocular lens to an existing artificial intraocular lens to correct for ongoing degradation of vision. That is, if the ability of the eye to focus grows worse over time, instead of replacing the entire intraocular lens with a new intraocular lens having a different refractive power, a supplemental intraocular lens can be attached to the existing intraocular lens. This technique is less invasive and hence, less traumatic to the eye.

U.S. Pat. No. 6,197,057, the entire contents of which are herein incorporated by reference, relates to a lens system that combines a high plus lens with a plus and minus intraocular lens (IOL), so that the lens system works in a manner similar to a Galilean telescope. Generally the high plus lens is outside the eye (i.e. in glasses or spectacles or in a contact lens) and the plus and minus lens is an IOL that replaces or works in conjunction with the natural lens of the patient (See FIGS. 1 and 2).

Additionally, if desired, the plus and minus lens can have a high minus portion in the center of the eye, while the portions surrounding the minus portion have no power, i.e., the surrounding portion can be flat.

The 'Peyman '057 patent also discloses a supplemental intraocular lens that can be attached to the natural lens or an existing artificial lens to make the lens adaptable to function as a teledioptic or diffractive prismatic lens of the type described above.

Accordingly, a continuing need exists for a supplemental intraocular and intracorneal lenses that can improve the vision in the eye.

SUMMARY OF THE INVENTION

An object of the invention is to provide a supplemental intraocular lens for modifying the natural lens or an existing artificial lens in an eye to correct for macular degeneration.

Another object of the present invention is to provide an intraocular lens for implantation in the eye to modify the lens system of the eye comprising the cornea and the natural or existing artificial lens in the eye, to create a lens system that functions as a teledioptic lens system which, when used without an external lens, provides unmagnified and peripherally unrestricted vision and which, when used with an external lens, provides magnified and peripherally restricted vision to correct for macular degeneration.

A further object of the invention is to provide intraocular lenses of the types described above which further include fastening members which enable those intraocular lenses to be secured in the eye.

A still further object of the invention is to provide intraocular lenses of the type described above which are capable of being secured directly in front of the surface of the natural or existing artificial lens in the eye.

Another object of the present invention is to provide a Galilean telescopic lens system to improve vision in the eye.

Yet a further object of the present invention is to provide a telescopic lens system for the eye, wherein one of the lenses implanted in the cornea of the eye, so that the lens follows the natural direction of the eye.

The foregoing objects are basically attained by providing an intraocular lens system for implantation in the eye to modify the lens system of the eye comprising the cornea and the natural or existing artificial lens in the eye, comprising a lens having a high minus portion and an outer portion substantially surrounding the high minus portion and being formed as a plus, minus or toric lens, adapted to be implanted in the eye to create a lens system that functions as a teledioptic lens system which, when used without an external lens, provides unmagnified and peripherally unrestricted vision and which, when used with an external lens, provides magnified and peripherally restricted vision to correct for macular degeneration.

The foregoing objects are basically attained by providing a method for modifying the lens system of the eye comprising the cornea and the natural or existing artificial lens in the eye, the method comprising implanting in the eye a lens having a high minus portion and an outer portion substantially surrounding the high minus portion and being formed as a plus, minus or toric lens, to create a lens system that functions as a teledioptic lens system which, when used without an external lens, provides unmagnified and peripherally unrestricted vision and which, when used with an external lens, provides magnified and peripherally restricted vision to correct for macular degeneration.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE INVENTION

Figure 1:
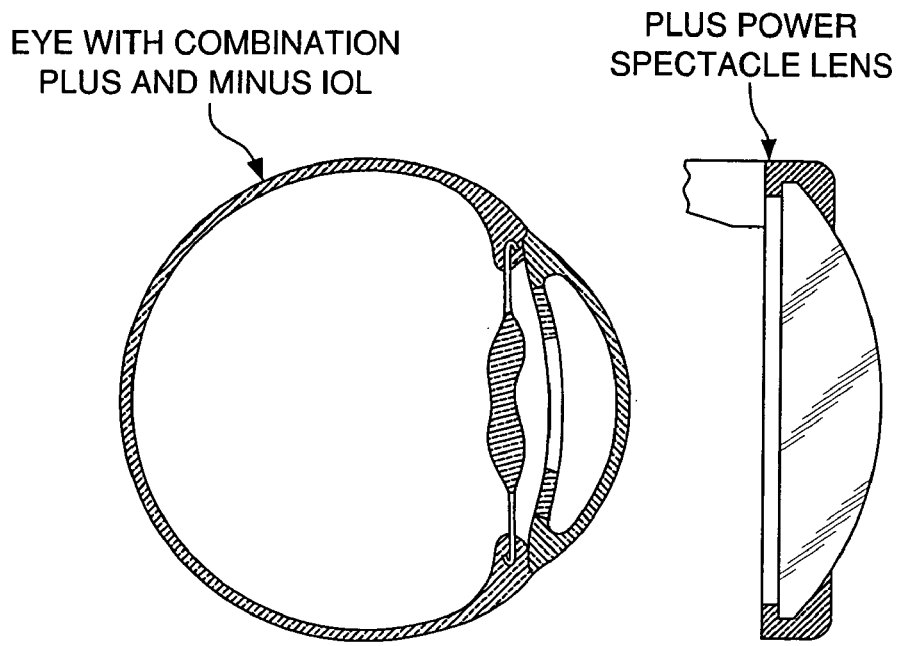
FIG. 1 illustrates the prior art wherein a plus lens is used outside the eye in conjunction with a combination plus and minus intraocular lens.
Figure 2:
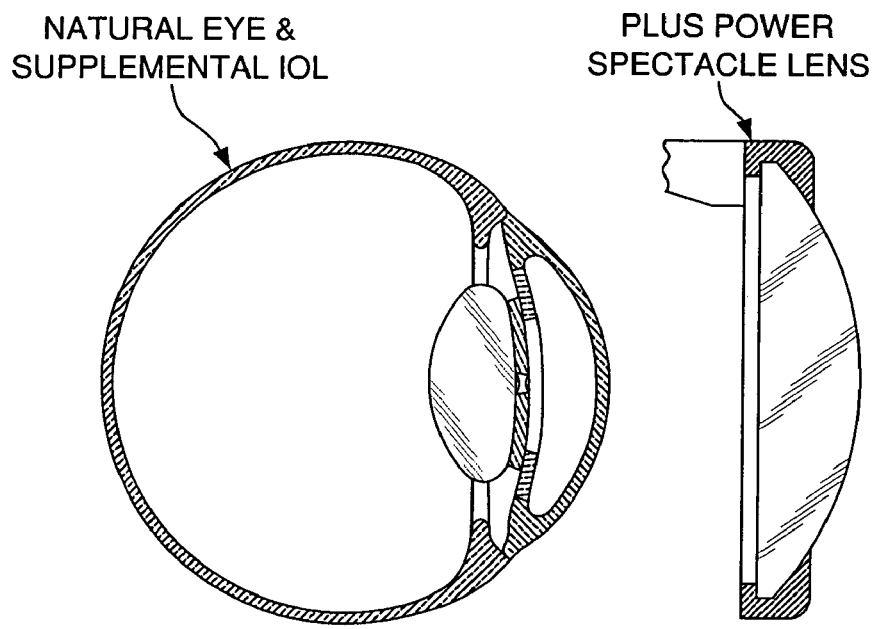
FIG. 2 illustrates the prior art wherein a plus lens is used outside the eye in conjunction with a lens having a minus portion and a portion with no refractive power.
Figure 3:
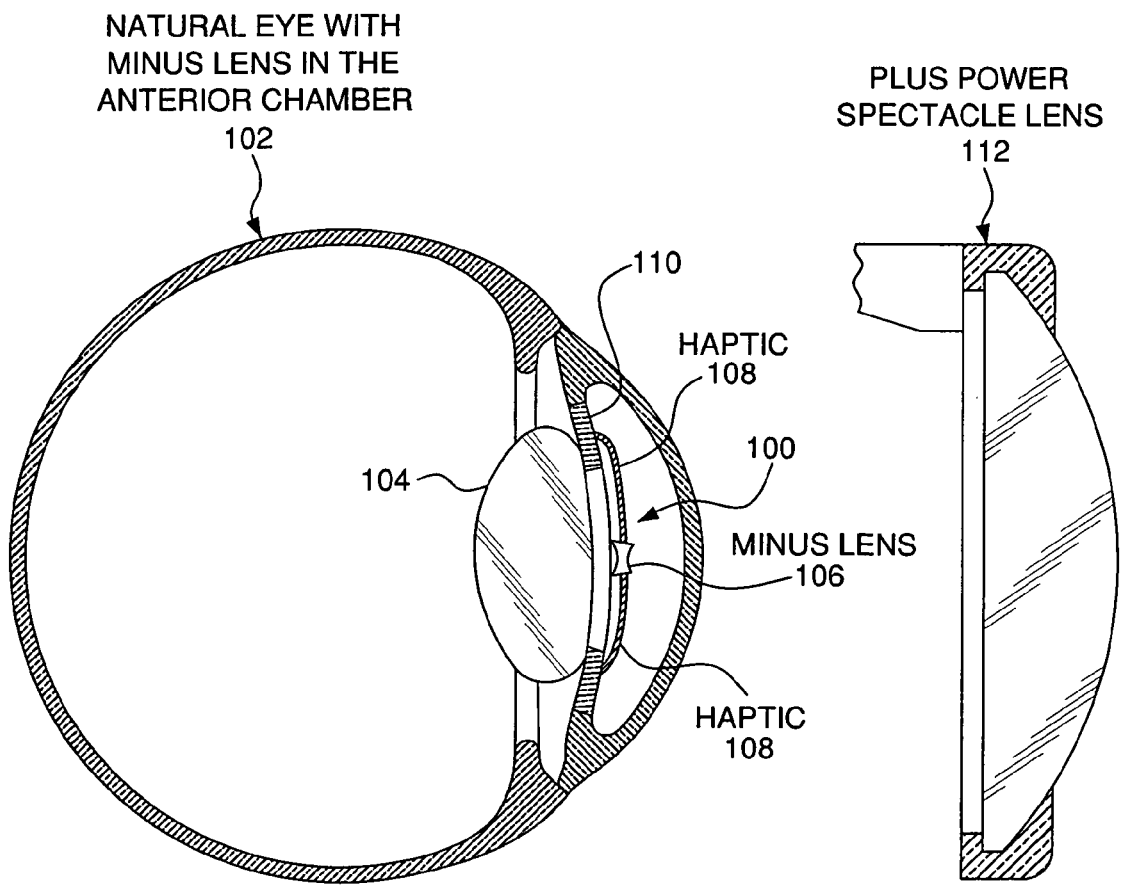
FIG. 3 illustrates a preferred embodiment of the present invention including an elevational side view in section of a plus lens outside the eye and a minus lens implanted in an anterior portion of the eye.
Figure 4:
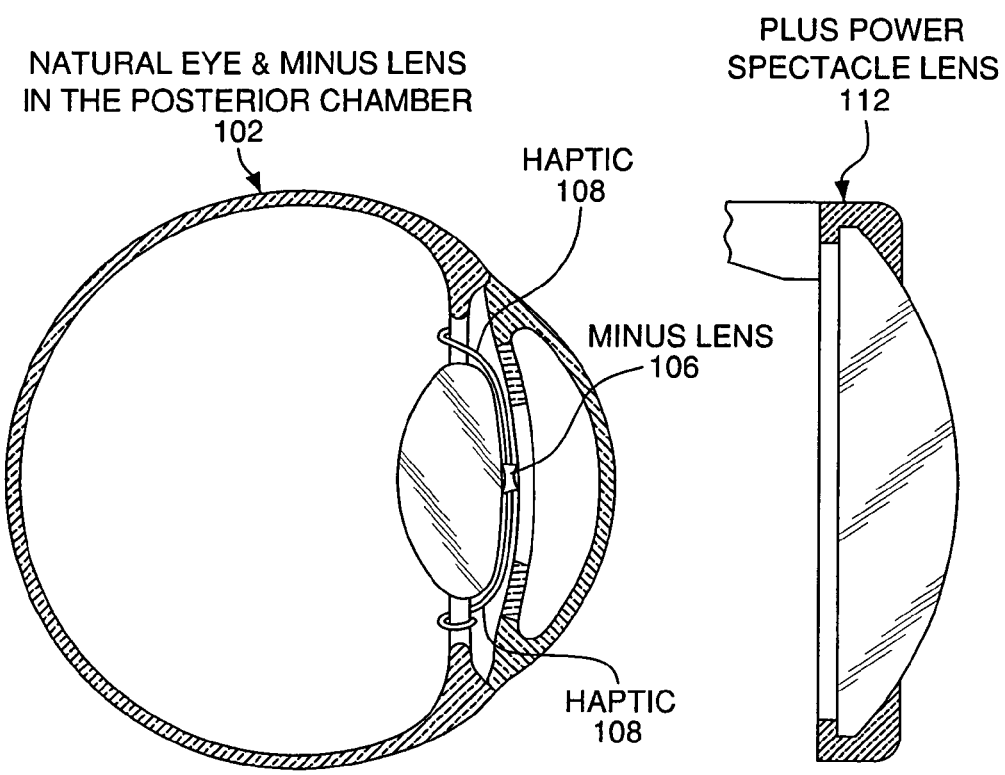
FIG. 4 is an elevational side view in section of a plus lens outside the eye and a minus lens implanted in a posterior chamber of the eye.

As illustrated in FIGS. 3 and 4, the preferred embodiment of the present invention includes a modified or miniaturized telescope 100 for the eye 102. More specifically, in conjunction with a patient's original lens 104 or in conjunction with an IOL, a miniaturized high minus lens 106 is affixed to an interior portion of the eye 102, the high minus lens 106 having an outer perimeter or free edge, as seen in FIGS. 3 and 4, with a diameter of about 1 millimeter to about 3 millimeters. Although using a high minus lens 106 is preferred, the lens 106 can be a minus diopter and not necessarily a high minus. The minus lens 106 can be affixed using any method desired, such as haptics 108, adhesive or in any other manner, and can be affixed to the iris 110, the angle, the zonular ligaments, the natural lens 104, or an IOL, or any other suitable portion of the eye 102. Additionally, the minus lens can be affixed in the posterior chamber or the anterior chamber of the eye.

Furthermore, a high plus lens or any other suitable lens is placed outside the eye 102 in spectacles or glasses 112 or as a contact lens and acts with the minus lens to produce a telescopic effect.

Figure 5:
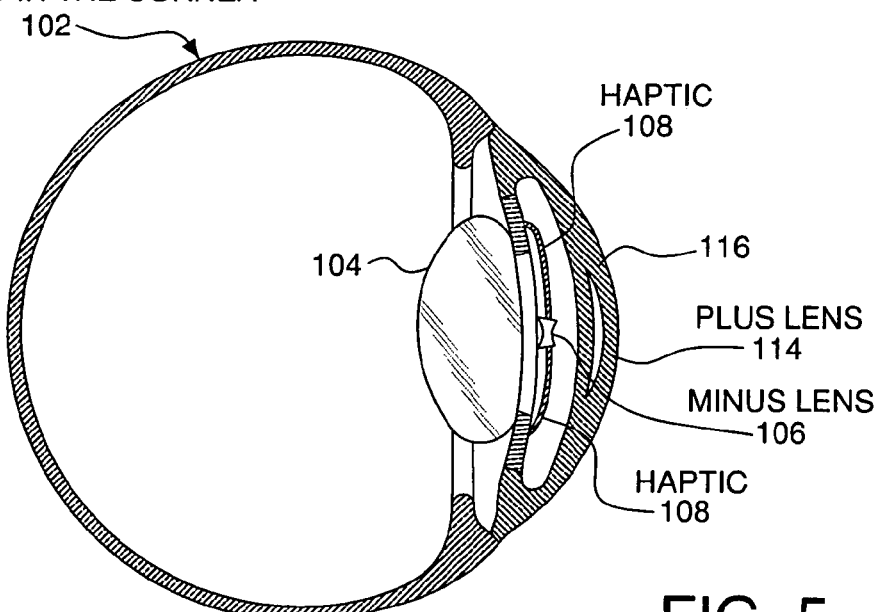
FIG. 5 is an elevational side view in section of a plus lens implanted in the cornea and a minus lens implanted in an anterior chamber of the eye.

In a further embodiment of the present invention, as shown in FIG. 5, the high plus lens 114 can be inserted into the cornea 116. The high plus lens can be implanted in the stroma, the epithelium, or any other portion of the cornea desired.

Figure 6:
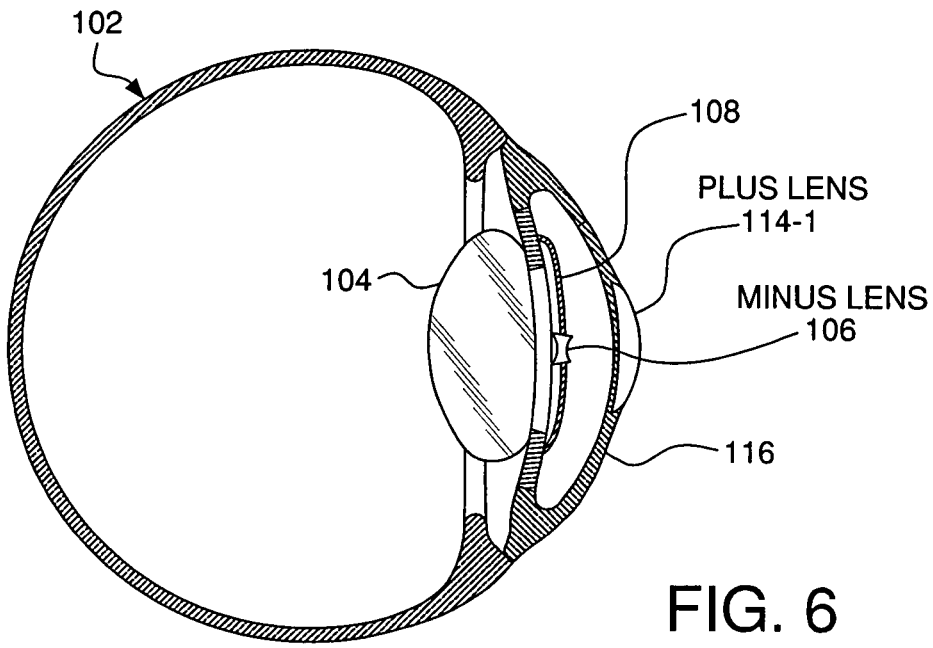
FIG. 6 is an elevational side view in section of a plus lens partially implanted in the cornea and a minus lens implanted in an anterior chamber of the eye.

By having the high plus lens 114 implanted in the cornea 116, or a contact lens, the lens 114 actually moves with the eye 102 and therefore reduces or eliminates any distortion. The high plus lens 114 can be inserted into the cornea in any manner desired. For example, the lens can be inserted under a flap or into a pocket formed in the cornea. Additionally, the inlay or high plus lens 114-1 can have a portion embedded in the cornea and a portion exposed and not covered by a layer of the cornea (FIG. 6).

Figure 7:
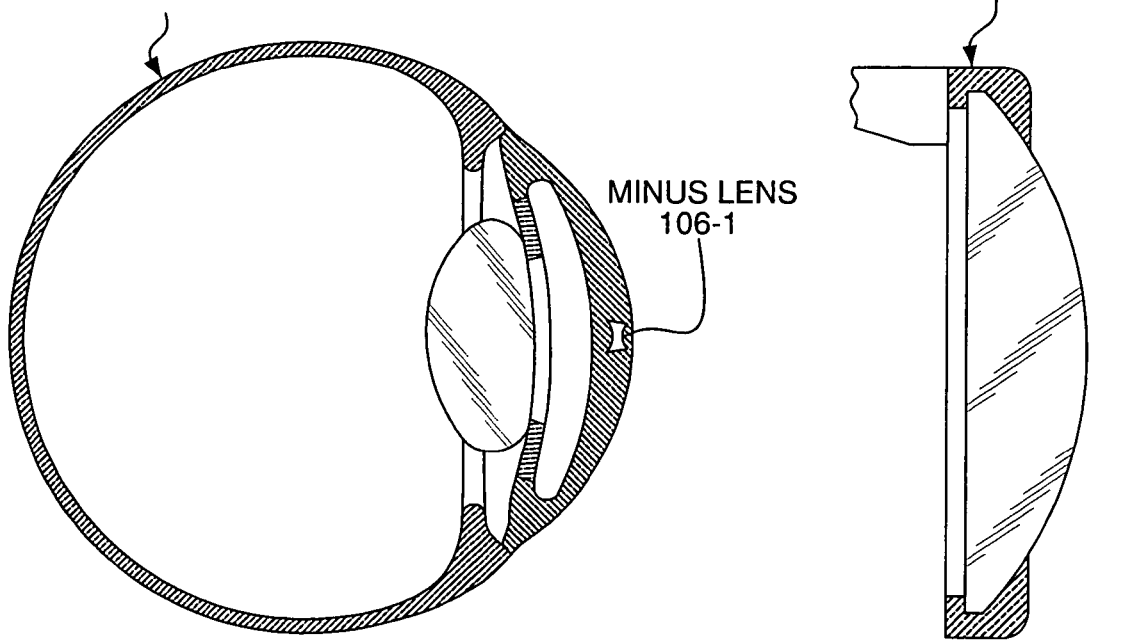
FIG. 7 is an elevational side view in section of a plus lens outside the eye and a minus lens implanted in the cornea.
Figure 8:
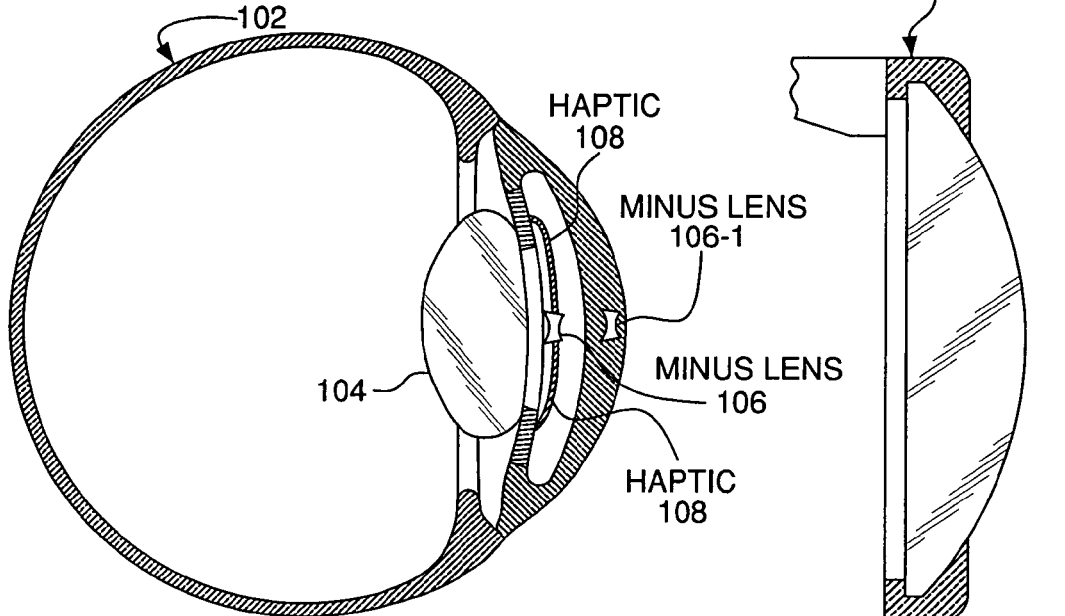
FIG. 8 is an elevational side view in section of a minus lens implanted in the cornea and a plus lens outside the eye in conjunction with a minus lens implanted in an anterior chamber of the eye.
Figure 9:
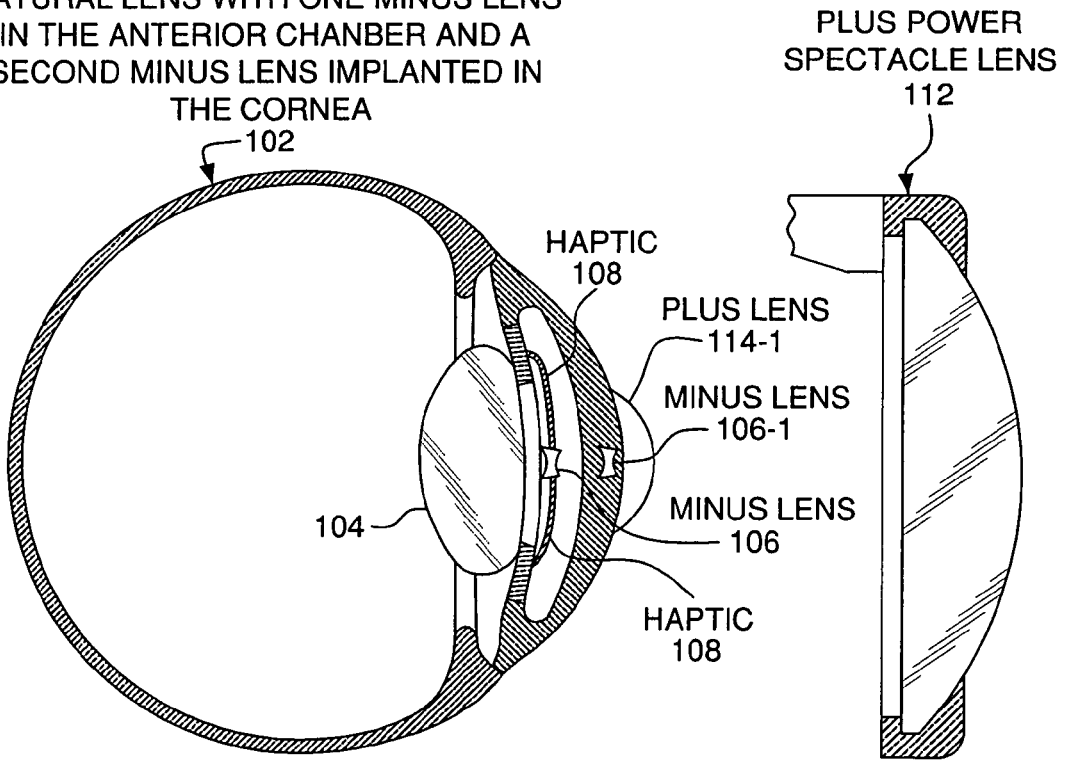
FIG. 9 is an elevational side view in section of two plus lenses, both outside the eye and two minus lenses, one minus lens in an anterior chamber of the eye and one minus lens implanted in the cornea of the eye.

Yet in another embodiment of the present invention, as shown in FIGS. 7–9, the minus lens 100-1 can be inserted into the cornea 116, as described above for the high plus lens and the high plus lens 114 can be positioned outside the cornea 116. For example, the minus lens 100-1 can be inserted under a flap or into a pocket formed in the cornea 116. Furthermore a portion of the minus lens 100-1 can be exposed, as described above, for the high plus lens.

Any of these embodiments can be combined to form a multiple lens system. For example, two plus lenses 112 and 114 can be used, one lens in the cornea 116 or partially in the cornea, as described above and a second lens outside the cornea in spectacles 112, glasses or contacts (FIG. 9). Additionally, two minus lenses 100 and 100-1 can be used, one lens 100-1 in the cornea 116, as described above, and one lens 100 in the anterior or posterior chamber of the eye 102, as described above, in conjunction with a high plus lens outside or inside the eye, as described above (FIGS. 8 and 9). The second minus lens can be affixed to the iris, the angle, the zonular ligaments, the natural lens or an IOL, or any other suitable portion of the eye. Furthermore, two plus lenses outside the eye in spectacles, glasses or contacts in any manner desired, along with the one or two minus lenses described herein.

Figure 10:
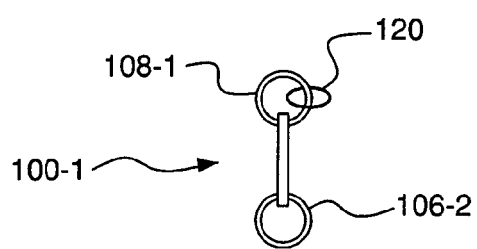
FIG. 10 is an elevational front view in section of a high minus lens having a sutured haptic.
Figure 11:
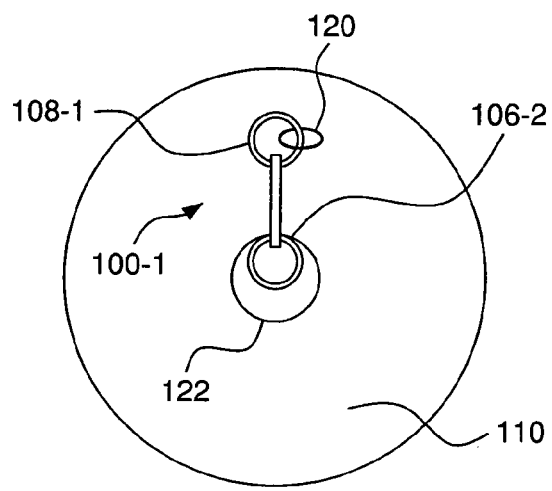
FIG. 11 is an elevational front view in section of a high minus lens in which the haptic is sutured to the iris.
Figure 12:
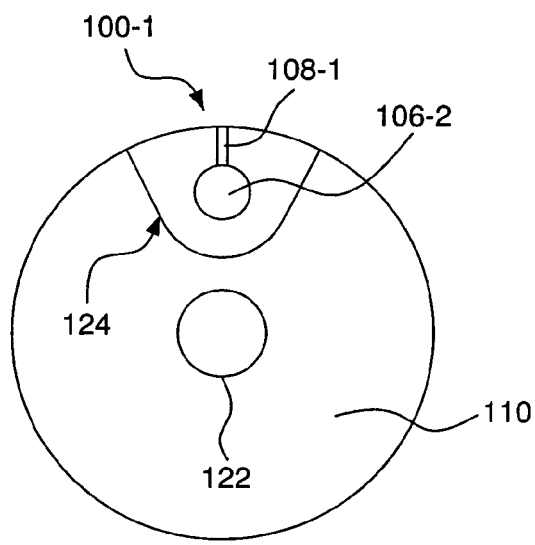
FIG. 12 is a front elevational view in section of a minus lens fixed to an outer portion of the iris by peripheral iridectomy.

Another embodiment is shown in FIGS. 10–12. As indicated, a lens structure 100-1 includes a lens 106-2 and a haptic 108-1. A suture 120 may be used to fix haptic 108-1 that is connected to lens 106-2 to the eye and, in particular, to the iris 110, as shown in FIG. 11. The lens 106-2, which can be a high minus lens as discussed above, can thus be positioned in the pupil 122. Alternatively, a high minus lens 106 may be inserted in the iris 110 by peripheral iridectomy, in which a section 124 is removed from the iris 110, as shown in FIG. 12. Preferably, lens 106-2 is used in conjunction with the telescopic system described above.

Figure 13:
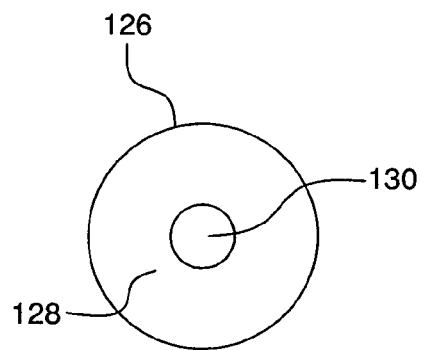
FIG. 13 is an elevational front view of an intraocular lens having a minus portion in the peripheral part of the lens and a plus portion in the central part of the lens.

Another preferred embodiment shown in FIG. 13 uses an intraocular lens (IOL) 126 having a minus portion 128 and a plus portion 130. Preferably, the minus portion 128 forms the periphery of the lens and surrounds a central plus portion 130. The plus portion 130 of the lens 126 corrects far vision, while the peripheral minus portion 128 acts in conjunction with an outside lens, such as one in spectacles, to produce a telescopic effect. The lens 126 may be employed as the lens 106 or 106-1 discussed above, and thus may be affixed to any suitable portion of the eye, such as the iris 110, lens 104, the angle, the zonular ligaments, or piggyback, such as is shown in FIGS. 3–6, 8 and 9 as discussed above. Additionally, the center portion can be a minus portion for the correction of myopia or a toric portion for the correction of an astigmatism, or any combination of a minus, plus or toric lens if desired.

Figures 14, 15, 16:
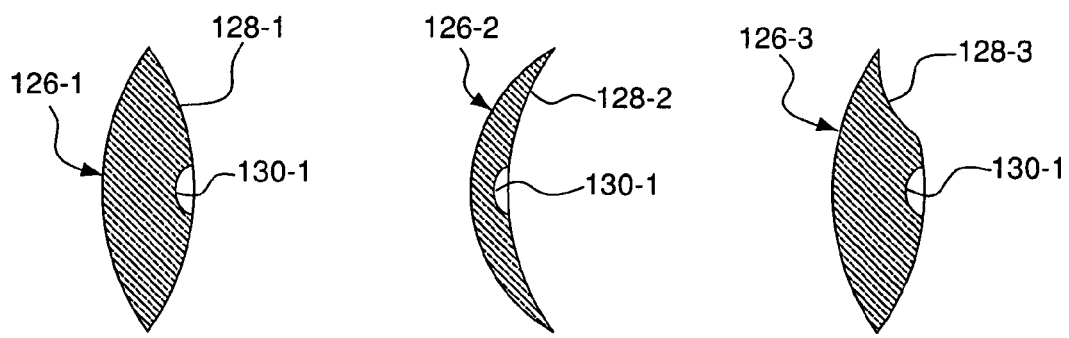
FIG. 14 is a side elevational in section of a lens having a high minus central portion for the correction of macular degeneration and a plus peripheral portion for the correction of hyperopia.
FIG. 15 is a side elevational in section of a lens having high minus central portion for the correction of macular degeneration and a minus peripheral portion for the correction of myopia.
FIG. 16 is a side elevational in section of a lens having a high minus central portion for the correction of macular degeneration and a toric peripheral portion for the correction of astigmatism.

Furthermore, FIGS. 14–16 illustrate three additional configurations of lens 126, lens 126-1, lens 126-2 and lens 126-3, respectively. In each of these configurations, the central portion of each lens can be a high minus portion 130-1 and the peripheral area or portion can be a plus portion 128-1, a minus portion 128-2 or a toric portion 128-3. The refractive power of portions 128-1, 128-2 and 128-3 are generally about plus or minus 2 diopters, but can be any power desired, depending on the required correction in the eye. Preferably, the high minus center portion 130-1 is used to correct for macular degeneration in conjunction with a secondary lens to achieve a telescopic effect, as described above, to allow the eye to focus on a close object for activities such as reading. The peripheral area or portions 128-1, 128-2 and 128-3 are used to correct a secondary problem, such as hyperopia, myopia and/or astigmatism, and are generally used without a secondary lens, although they can be used with a secondary lens, if so desired.

Preferably, lens 126-1 is used in conjunction with the telescopic system described herein and with the natural lens of the eye, an existing IOL that replaces the natural lens in the eye, or an IOL that works in conjunction with the natural lens in the eye.

By forming portions 128-1, 128-2 and 128-3 in the manner described herein, not only can macular degeneration be corrected, but so can a secondary type of vision disorder, such as myopia, hyperopia and/or astigmatism with the same lens. This reduces the number of procedures and/or lenses that are implanted in the eye.

It is noted that lenses 126 and 126-1 can be any type of lens desired. For example, lenses 126 and/or 126-1 can be implanted in the eye while connected to the iris as shown in FIGS. 11 and 12, each can be implanted in the cornea, similar to the lenses shown in FIGS. 5–9, each can piggyback with existing an IOL, or can be coupled to an interior portion of the eye in any conventional manner relative to the natural lens in the eye. Additionally, lenses 126 and/or 126-1 can be positioned in the eye and replace any lens shown herein. For example, lens 126 and/or 126-1 can replace lens 106, lens 114, lens 114-1, and lens 106-1, in FIGS. 3–9.

It is further noted that any lens used and described herein can be made of synthetic material, organic material, or a combination of both synthetic and organic material, that permits all or substantially all light having a wavelength in the visible spectrum to pass through. Additionally, if desired, the lens can be formed of material that absorbs all or substantially all light having a wavelength in a laser light spectrum. For example, the lenses described herein can be made of collagen, copolymer collagen, polyethylene oxide, polypropylene, polyproledine or hydrogel, or cross-linked organic material such as collagen, hyaluronic acid, mucopolysaccharide or glycoprotein, to name a few. Preferably, each lens is porous to allow oxygen and nutrients to pass therethrough. Also, each lens can be made from a donor cornea of a human eye, or can be taken from a cultured cornea. However, the blank 18 is not limited to those materials, and can be made of any suitable material, such as those disclosed in U.S. Pat. No. 4,994,058 to Raven et al., U.S. Pat. No. 4,718,418 to L'Esperance, U.S. Pat. No. 5,336,261 to Barrett et al., U.S. Pat. No. 4,840,175 to Peyman, and a publication by Jose I. Barraquer, M.D. entitled "Keratomileusis and Keratophakia in the Surgical Correction of Aphakia", the disclosures of which are hereby incorporated by reference herein.

While preferred embodiments have been chosen to illustrate the invention, it will be understood by those skilled in the art that various changes and modifications can be made therein without departing from the scope of the invention as defined in the appended claims.

What is claimed is:

1. An intraocular lens system for implantation in the eye to modify the lens system of the eye comprising the cornea and the natural or existing artificial lens in the eye, comprising:
   a first lens having a high minus portion adapted to supplement the natural or existing artificial lens and be implanted in the eye; and
   a second lens adapted to be implanted into the eye in series with and anterior to said first lens and used in combination with said first lens to create a lens system that functions as a teledioptic lens system which, when used without an external lens, provides unmagnified and peripherally unrestricted vision and which, when used with an external lens, provides magnified and peripherally restricted vision to correct for macular degeneration;
   wherein the first lens includes a plus portion substantially surrounded by the high minus portion.

2. An intraocular lens system for implantation in the eye to modify the lens system of the eye comprising the cornea and the natural or existing artificial lens in the eye, comprising:
   a first lens having a high minus portion adapted to supplement the natural or existing artificial lens and be implanted in the eye; and
   a second lens adapted to be implanted into the eye in series with and anterior to said first lens and used in combination with said first lens to create a lens system that functions as a teledioptic lens system which, when used without an external lens, provides unmagnified and peripherally unrestricted vision and which, when used with an external lens, provides magnified and peripherally restricted vision to correct for macular degeneration;
   wherein the first lens includes a minus outer portion substantially surrounding the high minus portion.

3. An intraocular lens system for implantation in the eye to modify the lens system of the eye comprising the cornea and the natural or existing artificial lens in the eye, comprising:
   a first lens having a high minus portion adapted to supplement the natural or existing artificial lens and be implanted in the eye; and
   a second lens adapted to be implanted into the eye in series with and anterior to said first lens and used in combination with said first lens to create a lens system that functions as a teledioptic lens system which, when used without an external lens, provides unmagnified and peripherally unrestricted vision and which, when used with an external lens, provides magnified and peripherally restricted vision to correct for macular degeneration;
   wherein the first lens includes a plus outer portion substantially surrounding the high minus portion.

4. An intraocular lens system for implantation in the eye to modify the lens system of the eye comprising the cornea and the natural or existing artificial lens in the eye, comprising:
   a first lens having a high minus portion adapted to supplement the natural or existing artificial lens and be implanted in the eye; and
   a second lens adapted to be implanted into the eye in series with and anterior to said first lens and used in combination with said first lens to create a lens system that functions as a teledioptic lens system which, when used without an external lens, provides unmagnified and peripherally unrestricted vision and which, when used with an external lens, provides magnified and peripherally restricted vision to correct for macular degeneration;
   wherein the first lens includes a toric outer portion substantially surrounding the high minus portion.

5. A method for modifying the lens system of the eye comprising the cornea and the natural or existing artificial lens in the eye, the method comprising:
   implanting in the eye a first lens having a high minus portion; and
   implanting in the eye a second lens in series with and anterior to said first lens to create a lens system that supplements the natural or existing artificial lens and functions as a teledioptic lens system which, when used without an external lens, provides unmagnified and peripherally unrestricted vision and which, when used with an external lens, provides magnified and peripherally restricted vision to correct for macular degeneration.

6. A method as claimed in claim 5, further comprising:
   using at least one fastening member to secure the first lens to an interior portion of the eye.

7. A method as claimed in claim 6, wherein:
   the fastening member includes a haptic.

8. A method as claimed in claim 6, wherein:
   the using step uses the fastening member to secure the first lens to the iris of the eye.

9. A method as claimed in claim 8, wherein:
   the using step uses the fastening member to secure the first lens to the iris of the eye, such that the first lens aligns with the pupil of the eye.

10. A method as claimed in claim 8, wherein:
    the using step uses the fastening member to secure the first lens to the iris of the eye, such that the first lens is present in a portion of the iris that has been removed by iridectomy.

11. A method as claimed in claim 6, wherein:
    the using step uses the fastening member to secure the first lens in front of the surface of the natural or existing artificial lens in the eye.

12. A method as claimed in claim 5, wherein:
    implanting step implants the first lens in the cornea of the eye.

13. A method as claimed in claim 5, wherein:
    the first lens includes a plus portion substantially surrounded by the high minus portion.

14. A method as claimed in claim 5, wherein:
    the first lens includes a minus outer portion substantially surrounding the high minus portion.

15. A method as claimed in claim 5, wherein:
    the first lens includes a plus outer portion substantially surrounding the high minus portion.

16. A method as claimed in claim 5, wherein:
    the first lens includes a toric outer portion substantially surrounding the high minus portion.

17. A method as claimed in claim 5, wherein:
    the first lens, when used with the external lens, provides a Galilean telescopic lens system.

18. A method as claimed in claim 5, wherein
    said step of implanting the second lens into the eye includes implanting said second lens into the cornea of the eye, such that the first and second lenses form a teledioptic lens system.

19. An intraocular lens system for implantation in the eye to modify the lens system of the eye comprising the cornea and the natural or existing artificial lens in the eye, comprising:
- a first lens having a high minus portion and an outer portion substantially surrounding the high minus portion and being formed as a plus, minus, or toric lens, adapted to be implanted in the eye in a predetermined position relative to the natural lens or an existing artificial lens;
- a second lens adapted to be implanted into the eye anterior to the first lens and used in combination with said first lens to create a lens system that functions as a teledioptic lens system which, when used without an external lens, provides unmagnified and peripherally unrestricted vision and which, when used with an external lens, provides magnified and peripherally restricted vision to correct for macular degeneration.

20. A method for modifying the lens system of the eye comprising the cornea and the natural or existing artificial lens in the eye, the method comprising:
- implanting in the eye a first lens having a high minus portion and an outer portion substantially surrounding the high minus portion and being formed as a plus, minus or toric lens in a predetermined position relative to the natural or existing artificial lens in the eye,
- implanting in the eye a second lens in series with and anterior to said first lens to create a lens system that functions as a teledioptic lens system which, when used without an external lens, provides unmagnified and peripherally unrestricted vision and which, when used with an external lens, provides magnified and peripherally restricted vision to correct for macular degeneration.

* * * * *